(12) United States Patent
Kim et al.

(10) Patent No.: US 10,161,401 B2
(45) Date of Patent: Dec. 25, 2018

(54) COMPRESSOR AND METHOD OF AUTONOMOUSLY INSPECTING OIL

(71) Applicant: LG ELECTRONICS INC., Seoul (KR)

(72) Inventors: Taeshin Kim, Seoul (KR); Ikseo Park, Seoul (KR); Namsik Yim, Seoul (KR)

(73) Assignee: LG Electronics Inc., Seoul (KR)

( * ) Notice: Subject to any disclaimer, the term of this patent is extended or adjusted under 35 U.S.C. 154(b) by 184 days.

(21) Appl. No.: 14/926,879

(22) Filed: Oct. 29, 2015

(65) Prior Publication Data

US 2016/0123325 A1 May 5, 2016

(30) Foreign Application Priority Data

Oct. 30, 2014 (KR) .......................... 10-2014-0149212

(51) Int. Cl.
*G01F 1/68* (2006.01)
*G05D 7/06* (2006.01)
(Continued)

(52) U.S. Cl.
CPC .......... *F04C 28/28* (2013.01); *F04C 18/0215* (2013.01); *F04C 18/0223* (2013.01);
(Continued)

(58) Field of Classification Search
CPC .............. F04C 18/0215; F04C 18/0223; F04C 2240/809; F04C 2240/81; F04C 2270/24;
(Continued)

(56) References Cited

U.S. PATENT DOCUMENTS 6,167,719 B1 1/2001 Yakumaru et al.
2002/0134101 A1 9/2002 Gennami et al.
(Continued)

FOREIGN PATENT DOCUMENTS

JP H249989 2/1990
JP H9126177 5/1997
(Continued)

OTHER PUBLICATIONS

Korean Office action in application No. 10-2014-0149212 dated Apr. 1, 2016 (6 pages).
(Continued)

*Primary Examiner* — Audrey K Bradley
*Assistant Examiner* — Anthony Ayala Delgado
(74) *Attorney, Agent, or Firm* — Fish & Richardson P.C.

(57) ABSTRACT

Systems and techniques are disclosed to sense a temperature and a flow rate of oil in a compressor. A compressor includes: a casing; a frame on the casing; a fixed scroll on the frame; an orbiting scroll supported by the frame and defining a compression chamber while engaging the fixed scroll; and a crank shaft. The crank shaft transfers, to the orbiting scroll, a rotational force of a motor. The casing includes: a main housing including a refrigerant discharge passage and an oil passing passage; and a sub-housing including a refrigerant discharge port and an oil channel, which includes an oil reservoir, that each face the main housing. A sensor module attached to a sensor receptor in the sub-housing includes: a sensor housing covering the sensor receptor; and an oil sensor and a temperature sensor located on the sensor housing that each protrude towards the oil reservoir.

7 Claims, 8 Drawing Sheets

(51) Int. Cl.
*F04C 28/28* (2006.01)
*F04C 18/02* (2006.01)
*F04C 23/02* (2006.01)
*G01N 33/28* (2006.01)
*F04C 23/00* (2006.01)
*F04C 29/02* (2006.01)

(52) U.S. Cl.
CPC ............ *F04C 23/008* (2013.01); *F04C 23/02* (2013.01); *G01N 33/28* (2013.01); *F04C 29/025* (2013.01); *F04C 2240/809* (2013.01); *F04C 2240/81* (2013.01); *F04C 2270/24* (2013.01)

(58) Field of Classification Search
CPC ........ F04C 23/008; F04C 23/02; F04C 28/28; F04C 29/025
See application file for complete search history.

(56) References Cited

U.S. PATENT DOCUMENTS

| | | | |
|---|---|---|---|
| 2003/0082061 | A1 | 5/2003 | Funakoshi et al. |
| 2014/0044581 | A1* | 2/2014 | Mao ............... F04C 23/008 418/55.1 |
| 2015/0044082 | A1 | 2/2015 | Kiem |

FOREIGN PATENT DOCUMENTS

| | | |
|---|---|---|
| JP | 2002-285981 | 10/2002 |
| JP | 2002317785 | 10/2002 |
| KR | 10-2001-0035692 | 5/2001 |
| KR | 10-2008-0067263 | 7/2008 |
| KR | 10-2009-0071085 | 7/2009 |
| KR | 10-2013-0102356 A | 9/2013 |
| KR | 10-2014-0122557 | 10/2014 |
| WO | WO 2013/133550 A1 | 9/2013 |

OTHER PUBLICATIONS

Chinese Office Action in Chinese Application No. 201510621884.7, dated Jun. 12, 2017, 19 pages (with English translation).

* cited by examiner

COMPRESSOR AND METHOD OF AUTONOMOUSLY INSPECTING OIL

CROSS-REFERENCE TO RELATED APPLICATIONS

The present application claims the benefit of an earlier filing date and right of priority to Korean Patent Application Number 10-2014-0149212, filed on Oct. 30, 2014, the entire contents of which are incorporated herein by reference.

TECHNICAL FIELD

The present application relates to a compressor and a method of autonomously inspecting oil.

BACKGROUND

In general, a compressor is a mechanical device that compresses gas and generates increased pressure.

A compressor is typically installed in consumer electronics such as refrigerators, air conditioners, or vehicles and functions to compress a refrigerant. A compressor may be connected with a condenser and an evaporator to compress a refrigerant evaporated by the evaporator and supply the compressed refrigerant to the condenser.

There are various types of compressors such as reciprocating compressors, scroll compressors, and screw compressors. In the case of a scroll compressor, a pair of compression members, or scrolls, with three-dimensional involute curves may compress the refrigerant while gradually decreasing a volume in a space therebetween. Such scroll compressors may have low-noise and low-vibration properties, and as a result, may be suitable for use in consumer electronics or vehicles that in which low-noise and low-vibration operation are desirable.

Oil may be accommodated at a lower side of the compressor, and an oil channel may be formed in the compressor that guides the oil to a compression unit. The oil flows to the compression unit through the oil channel, thereby reducing abrasion in the compression unit, and increasing the operational lifespan of the compressor.

SUMMARY

Systems and techniques are disclosed that provide a compressor configured to sense a temperature and a flow rate of oil in the compressor.

In one aspect, a compressor includes: a casing; a frame fixed on the casing; a fixed scroll fixed on the frame; an orbiting scroll supported by the frame and defining a compression chamber while engaging with the fixed scroll; and a crank shaft. The crank shaft is coupled to the orbiting scroll and is configured to transfer, to the orbiting scroll, a rotational force of a motor. The casing includes: a main housing including a refrigerant discharge passage and an oil passing passage; and a sub-housing including a refrigerant discharge port and an oil channel that each face the main housing, the oil channel including an oil reservoir. The compressor also includes a sensor module attached to a sensor receptor in the sub-housing, the sensor module including: a sensor housing covering the sensor receptor; and an oil sensor and a temperature sensor that are each located on the sensor housing and that each protrude towards the oil reservoir.

In some implementations, the compressor further includes: a partition wall located in at least one of the main housing or the sub-housing, the partition wall partitioning a space between the main housing and the sub-housing into a refrigerant discharge chamber at an upper side of the partition wall and an oil storage space at a lower side of the partition wall; and a communicating portion located at the partition wall and configured to allow the refrigerant discharge chamber and the oil storage space to be in communication with each other.

In some implementations, the oil passing passage faces the oil storage space, and the refrigerant discharge port and the refrigerant discharge passage face the refrigerant discharge chamber.

In some implementations, the sub-housing includes: a central portion that houses the oil reservoir, the central portion being recessed and protruding towards the main housing, and a partition wall extending from the central portion and separating a refrigerant discharge chamber at an upper side of the partition wall and an oil storage space at a lower side of the partition wall.

In some implementations, the main housing includes: a central portion facing the oil reservoir and including a through passage through which a rotary shaft of the motor penetrates, a partition wall extending from the central portion and separating a refrigerant discharge chamber at an upper side of the partition wall and an oil storage space at a lower side of the partition wall, and a communicating portion located at the partition wall and configured to allow the refrigerant discharge chamber and the oil storage space to be in communication with each other.

In some implementations, the motor includes: a motor shaft including an inner channel into which the oil in the oil reservoir flows; and an oil pump located on the motor shaft, wherein the sensor module faces the inner channel.

In some implementations, the oil channel includes a vertical channel that is elongated at a lower side of the oil reservoir in a vertical direction and that is configured to guide the oil to the oil reservoir.

In some implementations, the compressor further includes a fixing ring located on the sensor housing and configured to fix the sensor housing to the sub-housing.

In another aspect, a compressor includes: a casing; a frame fixed on the casing; a fixed scroll fixed on the frame; an orbiting scroll supported by the frame and defining a compression chamber while engaging with the fixed scroll; a crank shaft coupled to the orbiting scroll and configured to transfer, to the orbiting scroll, a rotational force of a motor; an oil reservoir and an oil injection channel located in the frame, the oil injection channel configured to guide the oil in the oil reservoir to the compression chamber; and a sensor module. The sensor module is attached to a sensor receptor in the frame, and includes: a sensor housing covering the sensor receptor; and an oil sensor and a temperature sensor that are each located on the sensor housing and that each protrude towards the oil reservoir.

In some implementations, the frame includes: an inner frame including the oil reservoir and the oil injection channel; and an oil cover coupled to the inner frame and covering the oil reservoir, wherein the sensor receptor is located in the inner frame.

In another aspect, a compressor includes: a compression chamber; a casing surrounding the compression chamber and configured to accommodate oil at a lower side of the casing; an oil recovery channel configured to guide, to the compression chamber, the oil that is accommodated at the lower side of the casing, the oil recovery channel including at least one oil reservoir; and a sensor module. The sensor module is attached to a sensor receptor in the at least one the oil reservoir, and includes: a sensor housing covering the sensor receptor; and an oil sensor and a temperature sensor that are each disposed on the sensor housing and that each protrude towards the at least one oil reservoir.

In another aspect, a method of autonomously inspecting oil in a compressor is disclosed. The method includes: sensing oil by an oil sensor of a sensor module that is located in an oil reservoir in the compressor; sensing a temperature by a temperature sensor of the sensor module; and determining an amount of the oil sensed by the oil sensor. The method further includes determining that: the amount of the oil sensed by the oil sensor is less than a predetermined value, the temperature sensed by the temperature sensor is within a predetermined range, and a time duration, during which the oil sensed by the oil sensor is less than a predetermined value, is greater than or equal to a predetermined time duration. The method further includes transmitting, to an outside of the compressor, an indication of an abnormal state of the oil based on the determination that the amount of the oil sensed by the oil sensor is less than the predetermined value, the temperature sensed by the temperature sensor is within the predetermined range, and the time duration, during which the oil sensed by the oil sensor is less than a predetermined value, is greater than or equal to the predetermined time duration.

In some implementations, the method further includes: determining that the amount of the oil sensed by the oil sensor is less than the predetermined value, and the temperature sensed by the temperature sensor is outside of the predetermined range; and transmitting, to the outside of the compressor, an indication of the abnormal state of the oil based on the determination that the amount of the oil sensed by the oil sensor is less than the predetermined value, and the temperature sensed by the temperature sensor is outside of the predetermined range.

In some implementations, the method further includes: determining that the amount of the oil sensed by the oil sensor is greater than or equal to the predetermined value; and operating the compressor in a normal operation mode based on the determination that the amount of the oil sensed by the oil sensor is greater than or equal to the predetermined value.

In some implementations, the method further includes: determining a temperature outside of the compressor; and changing the predetermined range for the temperature sensor based on the determined temperature outside of the compressor.

The details of one or more implementations are set forth in the accompanying drawings and the description below. Other features will be apparent from the description and drawings, and from the claims. The description and specific examples below are given by way of illustration only, and various changes and modifications will be apparent.

DETAILED DESCRIPTION

Systems and techniques are disclosed to sense a temperature and a flow rate of oil in a compressor. Such techniques and systems may help mitigate abrasion and improve reliability of a compressor.

If a compressor is operated in a scenario in which an insufficient amount of oil is available in the oil channel of the compressor, then this may cause problems such as abrasion or damage in the compressor.

Techniques and systems disclosed herein may offer an advantage that oil in the oil reservoir of the compressor may be more accurately sensed even if the compressor is tilted or rattles.

Such techniques and systems may also enable more accurate monitoring of an oil supply in the compressor by sensing an amount of oil and a temperature in the oil channel by using a single sensor module, thereby increasing reliability of the compressor.

Figure 1:
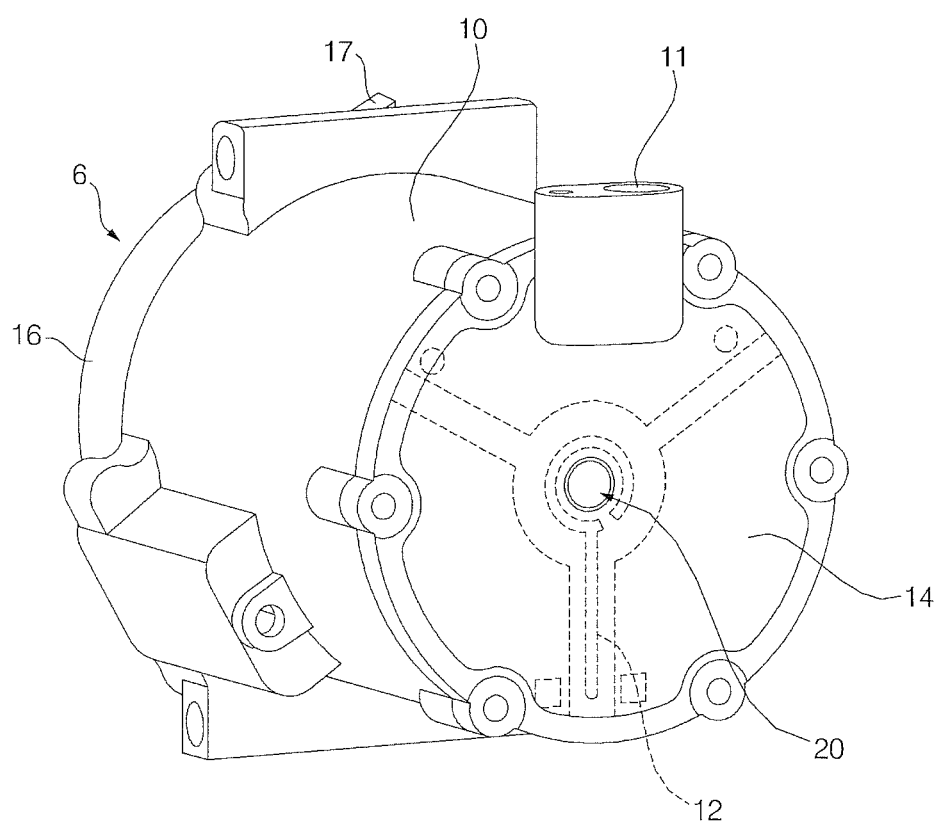
FIG. 1 is a diagram illustrating a perspective view of an example of a compressor.
Figure 2:
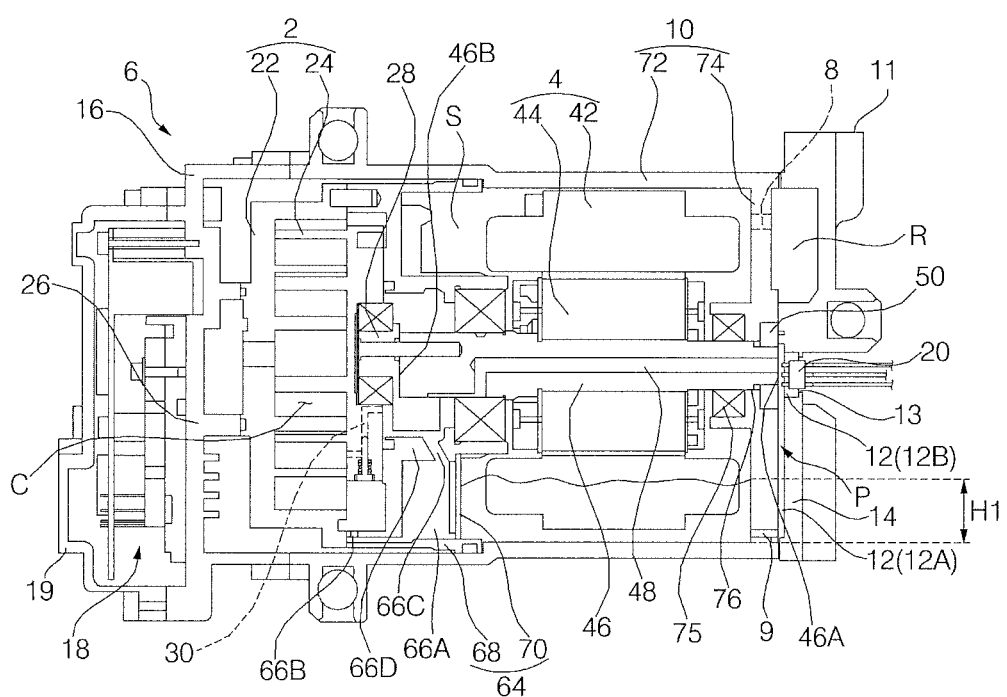
FIG. 2 is a diagram illustrating a cross-sectional view of the interior of an example of a compressor.
Figure 3:
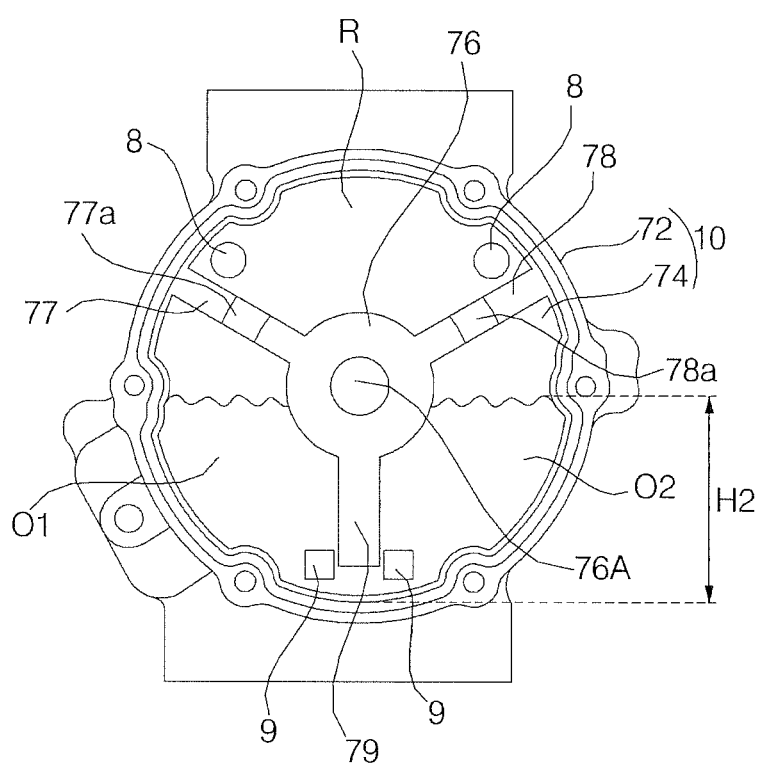
FIG. 3 is a diagram illustrating a side view of an example of a main housing of a compressor that faces a sub-housing of the compressor.
Figure 4:
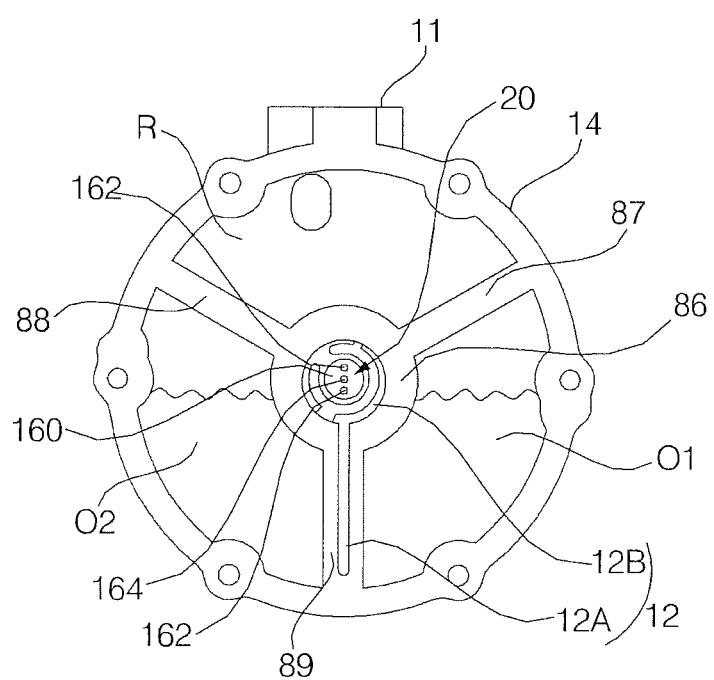
FIG. 4 is a diagram illustrating a side view of an example of a sub-housing of a compressor that faces a main housing of the compressor.
Figure 5:
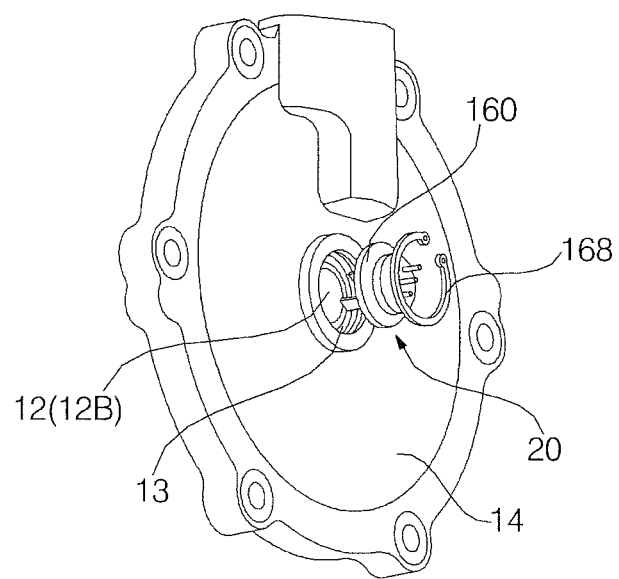
FIG. 5 is a diagram illustrating a detailed perspective view of an example of a sensor module of a compressor that is separated from a sub-housing of the compressor.
Figure 6:
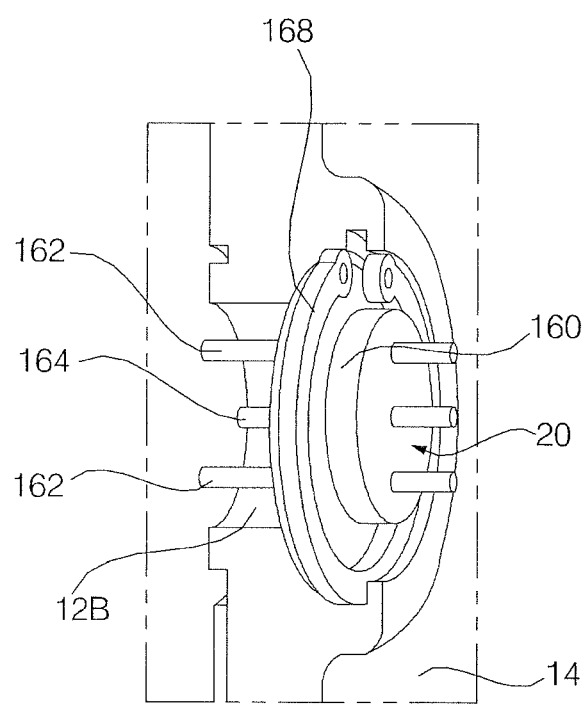
FIG. 6 is a diagram illustrating a partially cut-away cross-sectional view of an example of a sensor module of a compressor that is mounted to a sub-housing of the compressor.

FIG. 1 is a perspective view of a compressor, FIG. 2 is a cross-sectional view illustrating the interior of a compressor, FIG. 3 is a side view illustrating a side of a main housing of a compressor that faces a sub-housing of the compressor, FIG. 4 is a side view illustrating a side of a sub-housing of a compressor that faces a main housing of the compressor, FIG. 5 is an exploded perspective view illustrating a state in which a sensor module of a compressor is separated from a sub-housing of the compressor, and FIG. 6 is a partially cut-away cross-sectional view of a sensor module of a compressor that is mounted to a sub-housing of the compressor.

The compressor includes a compression unit 2 which has a compression chamber C that compresses a refrigerant, and a motor 4 which is connected to the compression unit 2. As an example, the compressor may be installed in a vehicle, and may be a compressor for a vehicle. In general, however, the compressor may be used for any suitable purpose in other types of systems.

The compressor may include a casing 6 that defines an external appearance of the compressor. Oil may be accommodated in the casing 6. The oil may be accommodated at a lower side in the casing 6. The compressor may be configured as a horizontal compressor that lies on its side in a horizontal direction. The casing 6 may be elongated in the horizontal direction.

The casing 6 may be configured as an assembly of a plurality of members. The casing 6 may include a main housing 10, and a sub-housing 14. The casing 6 may further include a cover 16 which is coupled to the main housing 10.

The main housing 10 may have a space S in which the compression unit 2 and the motor 4 are accommodated. A refrigerant discharge hole 8 and an oil passing hole 9 may be formed in the main housing 10. Oil may be accommodated in the space S of the main housing 10, and oil may be accommodated at a lower side in the main housing 10. Oil in the main housing 10 may move between the main housing 10 and the sub-housing 14 through the oil passing hole 9. The refrigerant compressed by the compression unit 2 may pass through the space S of the main housing 10, and the refrigerant may pass through the refrigerant discharge hole 8, and then may move between the main housing 10 and the sub-housing 14.

The sub-housing 14 may be installed to face the main housing 10. A refrigerant discharge port 11 and an oil channel 12 may be formed in the sub-housing 14. The sub-housing 14 may have an oil reservoir 12B formed in the oil channel 12. A sensor hole 13 in which a sensor module 20 to be described below is installed may be formed in the sub-housing 14. The sensor hole 13 may be formed to penetrate the sub-housing 14. The sensor module 20 may be mounted in the sensor hole 13, and may sense oil and temperature in the oil reservoir 12B. The refrigerant between the main housing 10 and the sub-housing 14 may be discharged to the outside of the compressor through the refrigerant discharge port 11. The oil between the main housing 10 and the sub-housing 14 may flow into the oil reservoir 12B while being guided to the oil channel 12, and the oil in the oil reservoir 12B may flow by the motor 4.

The cover 16 may be coupled to the main housing 10. The cover 16 may be coupled to the main housing 10 so as to be positioned at the opposite position to the sub-housing 14. The cover 16 may be configured as a single member, or may be configured as an assembly of a plurality of members. The cover 16 may be installed on the main housing 10 so as to surround a fixed scroll 22. A refrigerant intake port 17 may be formed in the cover 16.

The compressor may include an inverter 18 that controls the motor 4. The inverter 18 of the compressor may be mounted to the cover 16. The casing 6 may further include an inverter housing 19 that is coupled to the cover 16 and protects the inverter 18. A space, which accommodates the inverter 18, may be formed between the inverter housing 19 and the cover 16. The inverter 18 may be mounted to at least one of the cover 16 and the inverter housing 19.

The compressor may include the sensor module 20 installed on the sub-housing 14. The sensor module 20 may sense an amount of oil and a temperature in the oil reservoir 12B formed in the sub-housing 14.

The compressor may be configured as a scroll compressor in which the compression unit 2 has a pair of scrolls. The compression unit 2 may include the fixed scroll 22, and an orbiting scroll 24, and the compression chamber C may be formed between the fixed scroll 22 and the orbiting scroll 24.

The fixed scroll 22 may be installed to be positioned in the casing 6. A discharge hole 26 through which the refrigerant compressed in the compression chamber C is discharged to the outside of the compression unit 2 may be formed in the fixed scroll 22. The fixed scroll 22 may be installed on a frame 64 to be described below.

The orbiting scroll 24 may engage with the fixed scroll 22 and form the compression chamber C. The orbiting scroll 24 may be supported by the frame 64. The orbiting scroll 24 may be connected to a motor shaft 46 of the motor 4, which will be described below, through a crank shaft 28. The crank shaft 28 may be coupled to the orbiting scroll 24, and may transfer rotational force of the motor 4 to the orbiting scroll 24. When the motor 4 is operated, the orbiting scroll 24 may move relative to the fixed scroll 22 while being rotated eccentrically to the motor shaft 46. When the orbiting scroll 24 is rotated, the compression chamber C in the form of a crescent may be formed between the fixed scroll 22 and the orbiting scroll 24, and refrigerant vapor may be compressed (e.g., continuously) through a change in volume caused by the relative motion between the fixed scroll 22 and the orbiting scroll 24.

At least one orbiting scroll oil channel 30, through which the oil in an inner channel 48, which is formed in the motor shaft 46 and will be described below, is sucked and guided to the compression chamber C, may be formed in the orbiting scroll 24. The oil flowing into the inner channel 48 of the motor shaft 46 may flow between the fixed scroll 22 and the orbiting scroll 24 through the orbiting scroll oil channel 30, thereby minimizing abrasion between the fixed scroll 22 and the orbiting scroll 24.

The motor 4 may include an outer stator 42, and an inner rotor 44. Further, the motor 4 may further include the motor shaft 46. The motor shaft 46 may be installed on the inner rotor 44, and rotated together with the inner rotor 44 when the inner rotor 44 is rotated. The motor shaft 46 may have the inner channel 48 into which the oil in the oil channel 12 formed in the sub-housing 14 flows. One end of the inner channel 48 may face the oil reservoir 12B formed in the sub-housing 14. The motor 4 may include an oil pump 50 installed on the motor shaft 46.

The outer stator 42 may be installed in the casing 6. The outer stator 42 may be installed on an inner wall of the main housing 10. The outer stator 42 may be formed in a hollow shape.

The inner rotor 44 may be positioned inside the outer stator 42, and rotated by an interaction with the outer stator 42. The inner rotor 44 may be formed in a hollow shape.

The motor shaft 46 may be disposed to penetrate the inner rotor 44, and rotated together with the inner rotor 44 when the inner rotor 44 is rotated. One end 46A of the motor shaft 46 may face the sub-housing 14 of the casing 6, and the other end 46B thereof may be directed toward the compression unit 2.

The inner channel 48 may be elongated in a longitudinal direction of the motor shaft 46. One end of the inner channel 48 may face a part of the oil reservoir 12B, and the oil in the oil reservoir 12B may flow into the inner channel 48 through the one end of the inner channel 48, may pass through the inner channel 48, and then may be guided to the compression unit 2. The inner channel 48 may include a first channel which is elongated in the longitudinal direction of the motor shaft 46 from the one end 46A of the motor shaft 46, and a second channel which is formed in a circumferential direction of the motor shaft 46 from the first channel.

The oil pump 50 may be configured as a trochoid pump that is a kind of rotary pump, and the inner rotor with a trochoid curve may be installed on an outer circumference of the motor shaft 46. When the motor shaft 46 is rotated, the oil pump 50 may pump the oil in the oil channel 12, particularly, in the oil reservoir 12B to be described below, to the inner channel 48 of the motor shaft 46.

The compressor may include the frame 64 fixedly installed on the casing 6. The frame 64 may support the compression unit 2.

An outer circumference of the frame 64 may be fixed to an inner circumference of the main housing 10, such that the frame 64 may be disposed in the main housing 10.

A part of the frame 64 may be positioned between the main housing 10 and the cover 16, and the part, which is positioned between the main housing 10 and the cover 16, may be exposed to the outside of the compressor.

The frame 64 may be coupled to the fixed scroll 22, and may form, together with the fixed scroll 22, an orbiting scroll accommodating space in which the orbiting scroll 24 is accommodated.

An oil reservoir 66A, which is separated from the space S in the casing 6, and an oil injection channel 66B, which guides the oil in the oil reservoir 66A to the compression chamber C, may be formed in the frame 64. The oil reservoir 66A of the frame 64 may store the oil at a different location from the oil reservoir 12B of the sub-housing 14. An oil reservoir injection channel 66C, which guides the oil flowing out from the inner channel 48 of the motor shaft 46 to the oil reservoir 66A, may be formed in the frame 64. In a case in which the orbiting scroll oil channel 30 is formed in the orbiting scroll 22, an orbiting scroll injection channel 66D, which may guide the oil flowing out from the inner channel 48 of the motor shaft 46 to the orbiting scroll oil channel 30, may be further formed in the frame 64. Here, the oil reservoir 66A may be a space which accommodates the oil flowing out from the inner channel 48 of the motor shaft 46. The frame 64 may receive the oil flowing out from the inner channel 48 of the motor shaft 46, and guide the oil to the compression unit 2 through the oil injection channel 66B.

The frame 64 may include an inner frame 68 having the oil reservoir 66A and the oil injection channel 66B. The inner frame 68 may be fastened to the fixed scroll 22 to fix the fixed scroll 22, and may support the orbiting scroll 24. The frame 64 may include an oil cover 70 which is coupled to the inner frame 68 and covers the oil reservoir 66A.

Hereinafter, the main housing 10 and the sub-housing 14 will be described in detail below.

The main housing 10 may include a hollow tubular body 72, and a plate body 74.

The hollow tubular body 72 may have the space S which accommodates the outer stator 42 and the inner rotor 44.

The plate body 74 may face the frame 64. The plate body 74 may be a sub-housing opposing plate that faces the sub-housing 14.

A motor shaft bearing 75, which rotatably supports the motor shaft 46, may be installed on the plate body 74, and a rotary shaft through hole 76A, which the motor shaft 46 rotatably penetrates, may be formed.

The sub-housing 14 may be installed to face the plate body 74 of the main housing 10.

A refrigerant discharge chamber R, through which the refrigerant passing through the refrigerant discharge hole 8 passes to flow to the refrigerant discharge port 11, may be formed between the main housing 10 and the sub-housing 14.

The refrigerant compressed by the compression unit 2 may pass through the interior of the main housing 10 and the refrigerant discharge hole 8, may flow into the refrigerant discharge chamber R, and may flow from the refrigerant discharge chamber R to the refrigerant discharge port 11, and then may be discharged to the outside of the compressor. The refrigerant discharge chamber R may have lower pressure than the space S in the main housing 10.

Oil storage spaces O1 and O2, which may accommodate the oil passing through the oil passing hole 9, may be formed between the main housing 10 and the sub-housing 14.

When the motor shaft 46 is rotated, the oil in the oil storage spaces O1 and O2 may be pumped by the oil pump 50 and raised along the oil channel 12, and the oil may be pumped from the oil channel 12, particularly, the oil reservoir 12B to the inner channel 48 of the motor shaft 46.

The refrigerant discharge hole 8 may be formed to face the refrigerant discharge chamber R.

The refrigerant discharge hole 8 may be formed to penetrate an upper portion of the plate body 74 of the main housing 10.

The oil passing hole 9 may be formed to face the oil storage spaces O1 and O2. The oil passing hole 9 may be formed to penetrate a lower portion of the plate body 74 of the main housing 10.

The refrigerant discharge port 11 may be formed to face the refrigerant discharge chamber R. The refrigerant discharge port 11 may be formed in an upper portion of the sub-housing 14.

A partition wall, which partitions a space between the main housing 10 and the sub-housing 14 into the refrigerant discharge chamber R at the upper side and the oil storage spaces O1 and O2 at the lower side, may be formed on at least one of the main housing 10 and the sub-housing 14. Communicating portions 77a and 78a, which allow the refrigerant discharge chamber R and the oil storage spaces O1 and O2 to be in communication with each other, may be formed at a part of the partition wall. The communicating portions 77a and 78a may be portions for forming low pressure in the oil storage space, which allow the refrigerant discharge chamber R and the oil storage spaces O1 and O2 to be in communication with each other in order to allow the oil storage spaces O1 and O2 to have lower pressure than the space S.

In the compressor, among pressure P1 in the space S, pressure P2 in the oil storage spaces O1 and O2, and pressure P3 in the refrigerant discharge chamber R, the pressure P1 in the space S may be highest, the pressure P3 in the refrigerant discharge chamber R may be lowest, and the pressure P2 in the oil storage spaces O1 and O2 may be pressure between the pressure P1 in the space S and the pressure P3 in the refrigerant discharge chamber R. As illustrated in FIGS. 2 to 4, because the pressure P2 in the oil storage spaces O1 and O2 is lower than the pressure P1 of the space S, an oil level H2 in the oil storage spaces O1 and O2 may be higher than an oil level H1 in the space S, and there may be a height difference H2–H1 between the oil level H2 in the oil storage spaces O1 and O2 and the oil level H1 in the space S.

The main housing 10, particularly, the plate body 74 may include a central portion 76 which the rotary shaft 46 of the motor 4 penetrates and which has a through hole 76A that faces the oil reservoir 12B of the sub-housing 14.

Partition walls 77 and 78, which separate the refrigerant discharge chamber R at the upper side and the oil storage spaces O1 and O2 at the lower side, may be formed in the main housing 10, particularly, the plate body 74. The partition walls 77 and 78 of the main housing 10 may extend from the central portion 76, and separate the refrigerant discharge chamber R at the upper side and the oil storage spaces O1 and O2 at the lower side. The partition walls 77 and 78 of the main housing 10 may be formed to protrude toward the sub-housing 14. The partition walls 77 and 78 of the main housing 10 may be upper partition walls positioned at the upper side of the main housing 10, and may be provided as a pair. The communicating portions 77a and 78a, which allow the refrigerant discharge chamber R and the oil storage spaces O1 and O2 to be in communication with each other, may be formed in a part of each of the partition walls 77 and 78 of the main housing 10. The communicating portions 77a and 78a may be configured as a stepped portion that is recessed in the partition walls 77 and 78 in a direction opposite to the sub-housing 14.

A lower partition wall 79, which partitions a space at the lower side of the partition walls 77 and 78 into the two oil storage spaces O1 and O2, may be formed in the main housing 10, particularly, the plate body 74 so as to protrude toward the sub-housing 14. The lower partition wall 79 may be a partition wall positioned at the lower side of the main housing 10, and a single partition wall may be elongated in an up and down direction.

The sub-housing 14 may include a central portion 86 in which the oil reservoir 12B is formed to be recessed and which protrudes toward the main housing 10. The sensor hole 13 may be formed to penetrate the oil reservoir 12B.

The sub-housing 14 may include partition walls 87 and 88 that separate the refrigerant discharge chamber R at the upper side and the oil storage spaces O1 and O2 at the lower side. The partition walls 87 and 88 of the sub-housing 14 may extend from the central portion 86 of the sub-housing 14, and separate the refrigerant discharge chamber R at the upper side and the oil storage spaces O1 and O2 at the lower side. The partition walls 87 and 88 of the sub-housing 14 may be formed to protrude toward the main housing 10. The partition walls 87 and 88 of the sub-housing 14 may be upper partition walls positioned at the upper side of the sub-housing 14, and may be provided as a pair.

A lower partition wall 89, which partitions a space at the lower side of the partition walls 87 and 88 into the two oil storage spaces O1 and O2, may be formed in the sub-housing 14 so as to protrude toward the main housing 10. The lower partition wall 89 may be a partition wall positioned at the lower side of the sub-housing 14, and a single partition wall may be elongated in the up and down direction.

The oil channel 12 may include a vertical channel 12A that is elongated in the up and down direction at the lower side of the oil reservoir 12B and guides the oil to the oil reservoir 12B. The oil channel 12 may include the vertical channel 12A at the lower side, and the oil reservoir 12B at the upper side, and the oil may be raised to the oil reservoir 12B along the vertical channel 12A, and then may flow from the oil reservoir 12B to the inner channel 48 of the motor shaft 46.

The vertical channel 12A may be elongated in the lower partition wall 89 of the sub-housing 14 in the up and down direction, and the oil in the oil storage spaces O1 and O2 may be raised to the oil reservoir 12B of the sub-housing 14 along a portion between the lower partition wall 79 of the plate body 74 and the lower partition wall 89 of the sub-housing 14.

The compressor may include an oil recovery channel P which guides the oil accommodated at the lower side in the casing 6 to the compression chamber C and has at least one of the oil reservoirs 12B and 66A, and the sensor module 20 which is installed in the oil reservoirs 12B and 66A, the oil reservoirs 12B and 66A may have the sensor hole 13, and the sensor module 20 may be mounted in the sensor hole 13.

Here, the oil recovery channel P may be a channel which guides oil supply from the lower side in the main housing 10 to the compression chamber C. The oil recovery channel P may be a channel that includes the oil passing hole 9 of the main housing 10, the oil channel 12 having the oil reservoir 12B, the inner channel 48 of the motor shaft 46, and the oil reservoir injection channel 66C, the oil reservoir 66A, and the oil injection channel 66B of the frame 64.

The sensor module 20 includes a sensor housing 160 which covers the sensor hole 13, an oil sensor 162 which is installed on the sensor housing 160 so as to protrude toward the oil reservoir 12B, and a temperature sensor 164 which is installed on the sensor housing 160 so as to protrude toward the oil reservoir 12B.

Two oil sensors 162 may be two cylindrical condensers that are installed to overlap each other, in which one oil sensor 162 may sense quality of the oil, and the other oil sensor 162 may sense an amount of oil. One of the two oil sensors 162 may be installed at a higher position than the other one, and the oil sensor 162, which is positioned at a relatively higher position, may measure an amount of oil.

The sensor module 20 may sense oil and a temperature at a position adjacent to the inner channel 48 of the motor shaft 46 so as to sense whether the oil is smoothly supplied to the inner channel 48 of the motor shaft 46 when the compressor is operated. The sensor module 20 may be installed to face the inner channel 48 of the motor shaft 46. The sensor module 20 may be disposed in the oil reservoir 12B, and may sense an amount of oil and a temperature in the oil reservoir 12B. The sensor module 20 may be installed at a position where the oil level is higher than the space S, e.g., in the oil reservoir 12B, and may more accurately sense an amount of oil and a temperature even though the compressor is tilted or rattles.

The sensor housing 160 may be positioned in the oil reservoir 12B, and installed to face the inner channel 48 of the motor shaft 46. The oil sensor 162 and the temperature sensor 164 may be installed to be positioned in the oil reservoir 12B, the oil sensor 162 may sense an amount of oil in the oil reservoir 12B, and the temperature sensor 164 may sense the temperature in the oil reservoir 12B.

The compressor may further include a fixing ring 168 which is installed on the sensor housing 160 and fixes the sensor housing 160 to the sub-housing 14. The sensor module 20 may be installed by being inserted into the sensor hole 13 from the outside of the sub-housing 14, and the fixing ring 168 may inhibit the sensor module 20 from being arbitrarily detached from the sub-housing 14.

The sensor module 20 may be connected to an engine control unit (ECU) for a vehicle through a signal line, and may output the sensed result to the ECU for a vehicle. The ECU for a vehicle may communicate with an HVAC (heating, ventilation, and air conditioning) controller for a vehicle, and may output signals for controlling the compressor to the HVAC controller for a vehicle. The ECU for a vehicle may communicate with a display or a buzzer that is installed in the vehicle, and may output a signal for informing of an abnormal state of the oil in the compressor using the display and the buzzer when the oil in the compressor is abnormal.

Figure 7:
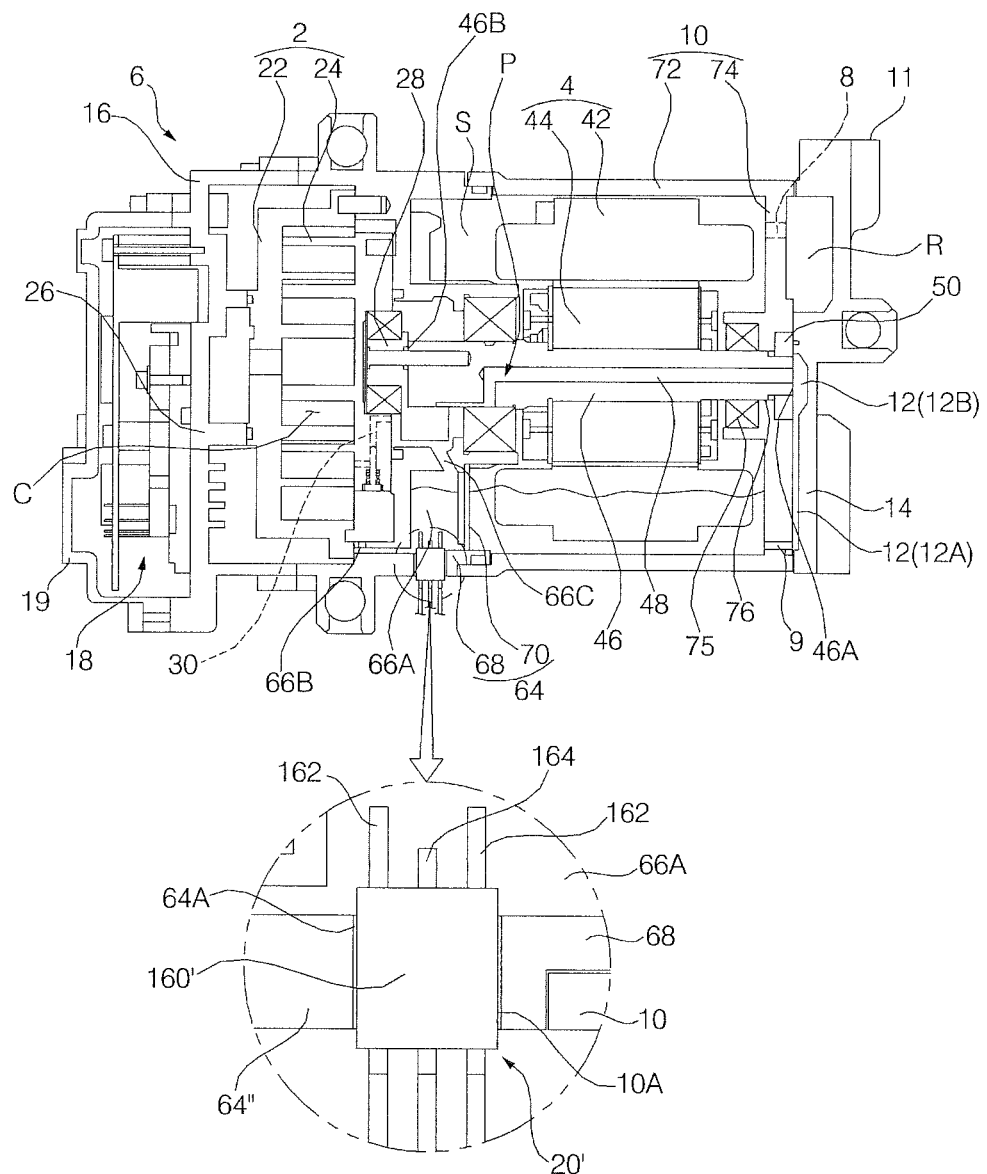
FIG. 7 is a diagram illustrating a cross-sectional view of an interior of an example of a compressor.

FIG. 7 is a cross-sectional view illustrating the interior of a compressor.

In the example shown in FIG. 7, an oil reservoir 66A, which is separated from the space S in the casing 6, and an oil injection channel 66B, which guides the oil in the oil reservoir 66A to the compression chamber C, may be formed in a frame 64', and a sensor hole 64A in which a sensor module 20' is installed may be formed in the frame 64'.

A part of the frame 64' may be installed to be exposed to the outside of the casing 6. A part 64'' of the frame 64' may be positioned between the main housing 10 and the cover 16, and the sensor module 20' may be mounted to the part 64'' of the frame 64', which is positioned between the main housing 10 and the cover 16. The sensor hole 64A may be formed to penetrate a portion 64'' of the frame 64' which is positioned between the main housing 10 and the cover 16, and the sensor module 20' may be installed to penetrate the frame 64'.

The sensor module 20' may include a sensor housing 160' which covers the sensor hole 64A formed in the frame 64', an oil sensor 162 which is installed on the sensor housing 160' so as to protrude toward the oil reservoir 66A, and a temperature sensor 164.

The frame 64' may include an inner frame 68' which has the oil reservoir 66A and the oil injection channel 66B, and an oil cover 70 which is coupled to the inner frame 68' and covers the oil reservoir 66A. The sensor hole 64A may be formed in the inner frame 68'. The sensor housing 162' may be installed on the frame 64' so as to cover the sensor hole 64A.

Figure 8:
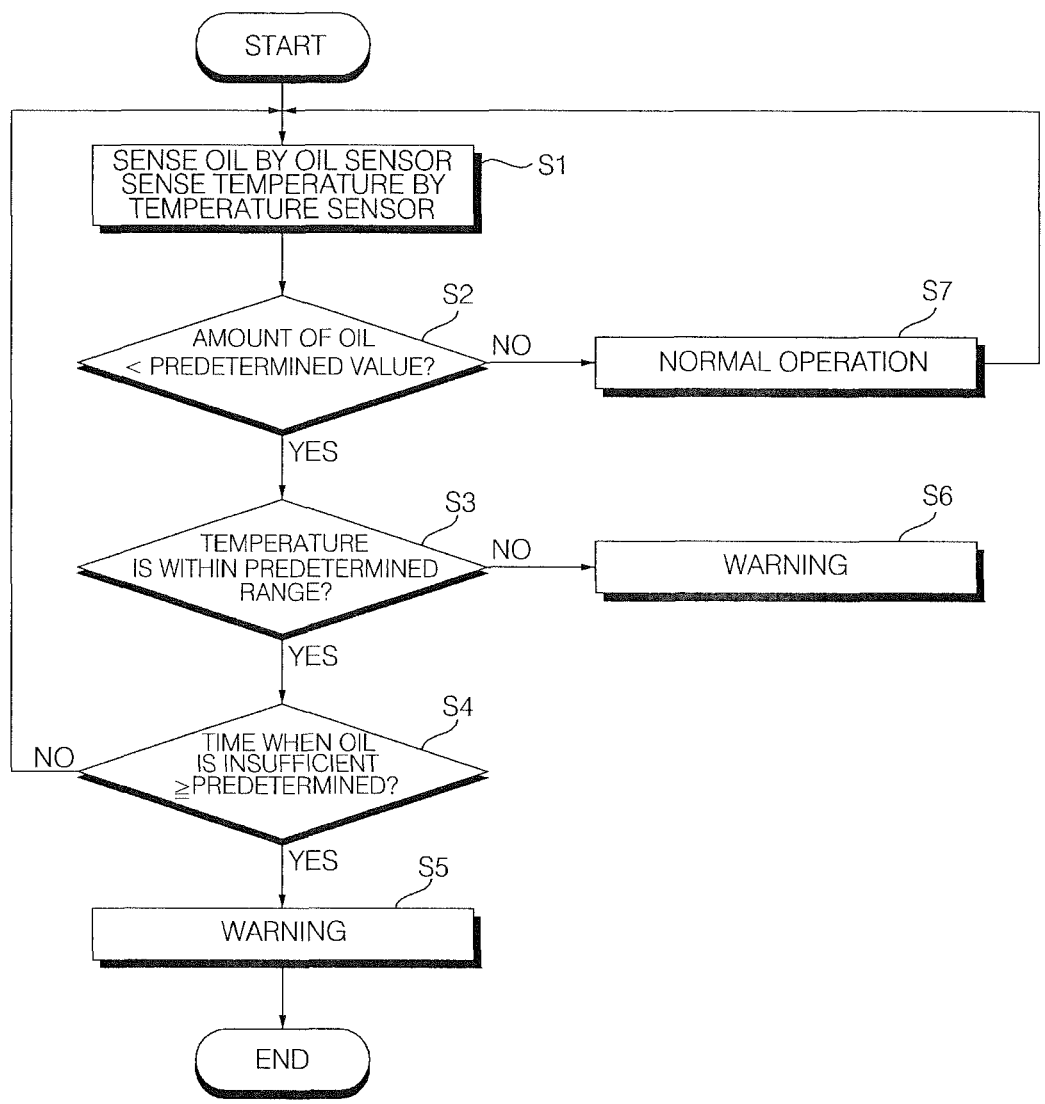
FIG. 8 is a flowchart illustrating an example of a method of autonomously inspecting oil in a compressor.

FIG. 8 is a flowchart illustrating a method of autonomously inspecting oil in the compressor.

A method of autonomously inspecting oil in the compressor may include sensing oil by the oil sensor 162 of the sensor module 20 installed in the oil reservoirs 12B or 66A formed in the compressor, and sensing a temperature by the temperature sensor 164 of the sensor module 20 (S1).

When the compressor is operated, the sensor module 20 may sense an amount of oil and an oil temperature in the oil reservoir 12B or 66A, and may output the sensed result to the ECU for a vehicle, and the ECU for a vehicle determines an abnormal state of the oil in the compressor based on the amount of oil and the oil temperature sensed by the sensor module 20.

The method of autonomously inspecting oil in the compressor may include informing the outside about an abnormal state of the oil when an amount of the oil sensed by the oil sensor 162 is less than a predetermined value, the temperature sensed by the temperature sensor 164 is within a predetermined range, and a time for which the oil is insufficient is a predetermined time or longer (S2, S3, S4, and S5).

Here, the predetermined value may be a reference for determining that the amount of oil is insufficient, and the ECU for a vehicle compares the amount of oil sensed by the oil sensor 162 with the predetermined value, and may determine that the oil in the oil reservoir 12B or 66A is currently insufficient when the amount of oil is less than the predetermined value.

The predetermined range may be a reference for determining whether a temperature in the oil reservoir 12B or 66A is excessive. The predetermined range may be changed by the outside temperature. The predetermined range may be set to be high when the outside temperature is high. The predetermined range may be set to be low when the outside temperature is low.

Further, the time for which the oil is insufficient may be a counted time for which the compressor is operated in a state in which the oil is insufficient in the compressor. The time for which the oil is insufficient may be counted from a point of time at which the insufficiency of the oil is sensed, and may be the time that is counted from a point of time at which a state in which the amount of oil is less than the predetermined value is sensed.

Further, the predetermined time may be a reference time that is set to determine whether to inform the outside about an abnormal state of the compressor.

In a case in which an amount of oil is less than the predetermined value and insufficient, or a time duration during which the temperature in the oil reservoir 12B or 66A is within a proper range is less than a predetermined time duration, the ECU for a vehicle may not inform the outside about an abnormal state of the oil. However, if the amount of oil is less than a predetermined value and insufficient, and a time duration during which a temperature in the oil reservoir 12B or 66A is within the proper range is greater than a predetermined time duration, the ECU for a vehicle may inform the outside about the insufficiency of the oil.

The ECU for a vehicle may output a control signal to a notification device such as a display or a buzzer, and the display or the buzzer may warn the outside about an abnormal state of the oil.

In some implementations, the method of autonomously inspecting oil in the compressor may include informing the outside about an abnormal state of the oil when an amount of the oil sensed by the oil sensor 162 is less than a predetermined value, and the temperature sensed by the temperature sensor 164 is outside of a predetermined range (S2, S3, and S6).

In a case in which the amount of oil is less than a predetermined value and insufficient, and the temperature in the oil channel 12 may deviate from a proper temperature range, the compressor may be damaged when the compressor is operated (e.g., continuously), and as a result, the ECU for a vehicle may output control signals by using a notification device such as a display or a buzzer, and may warn the outside about an abnormal state of the oil through a display or a buzzer, regardless of the operating time of the compressor or the time for which the oil is insufficient.

The method of autonomously inspecting oil in the compressor may include operating the compressor (S2 and S7) according to a normal operation mode when an amount of oil sensed by the oil sensor 162 is equal to or greater than a predetermined value.

As an example, a normal operation mode may be a scenario of driving a vehicle in which the compressor is operated according to signals from an HVAC control unit for the vehicle, and the compressor may be operated or stopped depending on loads in the interior of the vehicle. In a state in which the amount of oil sensed by the oil sensor 162 is equal to or greater than a predetermined value, the compressor may be operated when the interior of the vehicle is in a thermo-on condition, and the compressor may be stopped when the interior of the vehicle is in a thermo-off condition.

Implementations are not limited to configurations in which the compressor is a compressor for a vehicle or installed in a vehicle, as implementations should be understood to be applicable to other technical fields to which the present disclosure pertains.

Although the operations of the disclosed techniques may be described herein as being performed in a certain order and/or in certain combinations, in some implementations, individual operations may be rearranged in a different order, combined with other operations described herein, and/or eliminated, and desired results still may be achieved. Similarly, components in the disclosed systems may be combined in a different manner and/or replaced or supplemented by other components and desired results still may be achieved.

What is claimed is:

1. A compressor comprising:
  a casing;
  a frame fixed on the casing;
  a fixed scroll fixed on the frame;
  an orbiting scroll supported by the frame and defining a compression chamber while engaging with the fixed scroll; and
  a crank shaft coupled to the orbiting scroll and configured to transfer, to the orbiting scroll, a rotational force of a motor,
  wherein the casing comprises:
    a main housing comprising a refrigerant discharge passage and an oil passing passage; and a sub-housing comprising a refrigerant discharge port and an oil channel that each face the main housing, the oil channel including an oil reservoir, wherein the sub-housing comprises:
  a first central portion that houses the oil reservoir; and
  a first partition wall extending from the first central portion and separating a refrigerant discharge chamber at an upper side of the first partition wall and an oil storage space at a lower side of the first partition wall,
a sensor module attached to a sensor receptor in the sub-housing, the sensor module comprising:
  a sensor housing covering the sensor receptor; and
  an oil sensor and a temperature sensor that are each located on the sensor housing and that each protrude towards the oil reservoir.

2. The compressor of claim 1, further comprising:
a first communicating portion located at the first partition wall and configured to allow the refrigerant discharge chamber and the oil storage space to be in communication with each other.

3. The compressor of claim 2, wherein the oil passing passage faces the oil storage space, and the refrigerant discharge port and the refrigerant discharge passage face the refrigerant discharge chamber.

4. The compressor of claim 1, wherein the main housing comprises:
  a second central portion facing the oil reservoir and including a through passage through which a rotary shaft of the motor penetrates,
  a second partition wall extending from the second central portion and separating the refrigerant discharge chamber at an upper side of the second partition wall and the oil storage space at a lower side of the second partition wall, and
  a second communicating portion located at the second partition wall and configured to allow the refrigerant discharge chamber and the oil storage space to be in communication with each other.

5. The compressor of claim 1, wherein the motor comprises:
  a motor shaft including an inner channel into which the oil in the oil reservoir flows; and
  an oil pump located on the motor shaft,
wherein the sensor module faces the inner channel.

6. The compressor of claim 1, wherein the oil channel includes a vertical channel that is elongated at a lower side of the oil reservoir in a vertical direction and that is configured to guide the oil to the oil reservoir.

7. The compressor of claim 1, further comprising:
  a fixing ring located on the sensor housing and configured to fix the sensor housing to the sub-housing.

* * * * *